US010055552B2

(12) United States Patent
Cizmarik

(10) Patent No.: US 10,055,552 B2
(45) Date of Patent: Aug. 21, 2018

(54) PHARMACEUTICAL MANAGEMENT SYSTEM

(71) Applicant: TORViC Technologies, Inc., Stouffville (CA)

(72) Inventor: Vic Cizmarik, Stouffville (CA)

(73) Assignee: TORViC Technologies, Inc., Stouffville (CA)

(*) Notice: Subject to any disclaimer, the term of this patent is extended or adjusted under 35 U.S.C. 154(b) by 530 days.

(21) Appl. No.: 14/254,551

(22) Filed: Apr. 16, 2014

(65) Prior Publication Data

US 2014/0310018 A1 Oct. 16, 2014

Related U.S. Application Data

(60) Provisional application No. 61/812,480, filed on Apr. 16, 2013.

(51) Int. Cl.

| G06F 19/00 | (2018.01) |
|---|---|
| A61J 7/04 | (2006.01) |
| A61J 7/00 | (2006.01) |

(52) U.S. Cl.
CPC ........ *G06F 19/3462* (2013.01); *A61J 7/0084* (2013.01); *A61J 7/0418* (2015.05); *A61J 7/0436* (2015.05); *A61J 7/0481* (2013.01); *G16H 20/13* (2018.01); *G16H 40/40* (2018.01); *A61J 2200/30* (2013.01); *A61J 2205/20* (2013.01); *A61J 2205/70* (2013.01); *G06F 19/326* (2013.01); *G06F 19/328* (2013.01); *G16H 80/00* (2018.01)

(58) Field of Classification Search
CPC ...... G06Q 50/22; G06Q 50/24; G06F 19/322; G06F 19/324; G06F 19/3462; G06F 19/3456; G06F 19/326; G16H 20/10; G16H 20/13
See application file for complete search history.

(56) References Cited

U.S. PATENT DOCUMENTS

| 8,108,068 | B1* | 1/2012 | Boucher | A61J 7/0084 700/236 |
|---|---|---|---|---|
| 2002/0027507 | A1* | 3/2002 | Yarin | A61J 7/0481 340/573.1 |
| 2003/0164754 | A1* | 9/2003 | Roseen | F25D 25/00 340/309.16 |
| 2008/0052037 | A1* | 2/2008 | Bodin | G06Q 10/087 702/173 |
| 2009/0299522 | A1* | 12/2009 | Savir | A61J 7/0084 700/240 |
| 2012/0153031 | A1* | 6/2012 | Rupp | A61J 1/00 235/494 |

(Continued)

*Primary Examiner* — Jonathan Durant
(74) *Attorney, Agent, or Firm* — McMillan LLP

(57) ABSTRACT

A pharmaceutical management system including a housing having a closeable top cover. Within the housing, there is provided, in combination, a computer processor and a computer readable medium storing computer executable instructions being executed by the computer processor, a plurality of pharmaceutical containers within the housing; each of the plurality of pharmaceutical containers having an identification means, and scanning means in communication with the computer processor adapted to read information from the identification means. The computer executable instructions include instructions identifying a pharmaceutical in each of the containers based on information in the identification means.

17 Claims, 13 Drawing Sheets

(56) References Cited

U.S. PATENT DOCUMENTS

| | | | | |
|---|---|---|---|---|
| 2013/0002795 A1* | 1/2013 | Shavelsky | ............... | A61J 7/04 348/14.01 |
| 2013/0253700 A1* | 9/2013 | Carson | ................... | G07F 9/006 700/236 |
| 2014/0350720 A1* | 11/2014 | Lehmann | ............ | G06F 19/3462 700/236 |

* cited by examiner

PHARMACEUTICAL MANAGEMENT SYSTEM

FIELD OF THE INVENTION

The present invention relates generally to pharmaceutical management systems, and in particular to a portable pharmaceutical management system.

BACKGROUND OF THE INVENTION

Pharmaceutical containers for home use are well known in the art, including those that can store a plurality of medications in segments of the container for different days of the week, different weeks, and so forth. These types of containers assist a user or patient in staying organized with respect to which medications to take on which days. Furthermore, for those users being prescribed (or advised) to take a large number of different medications, these types of segmented containers attempt to ensure that the appropriate medications are taken on the appropriate days, and provides a user with an overview of when the prescription will run out, and another trip to the pharmacy may be in order.

In any event, these containers rely heavily on the user filling each segment properly, or in some cases another person filling the containers for the user.

Other users, who want to be able to reference the individual container of each of the medications simply line up each of the pharmaceutical containers for individual medications and take them on a regular schedule.

In either of these cases, a high degree of user involvement is required in either filling the segmented containers, or developing a personal system of remembering which medications to take at which times. In both cases, obtaining a refill on the prescription requires a user to actively monitor the number of pills remaining. With medications that are taken a number of times per day, this can be difficult. Furthermore, one or more of the above steps may be time consuming or difficult for patients with certain medical conditions. Patients who take a number may be prone to over or under medicating and there is a high risk of error that can lead to hospitalization or even death It is therefore an object of the invention to provide an improved pharmaceutical management system.

SUMMARY OF THE INVENTION

In accordance with an embodiment of the invention, there is provided a pharmaceutical management system having an integral computer system including a processor and providing for one or more of separate pharmaceutical pill containers, prescription storage, container labeling, capture and interpretation of labels, scanning of pharmaceutical container labels, pill counting or weighing capabilities, interaction capabilities with a pharmacist, user interaction via a touch screen, and computer readable instructions executed by a computer system to implement any of the above.

Accordingly, there is provided a pharmaceutical management system comprising a housing having a closeable top cover; the pharmaceutical management system including within the housing, in combination a computer processor and a computer readable medium storing computer executable instructions being executed by the computer processor; a plurality of pharmaceutical containers within the housing; each of the plurality of pharmaceutical containers having an identification means; and scanning means in communication with the computer processor adapted to read information from the identification means; wherein the computer executable instructions include instructions identifying a pharmaceutical in each of the containers based on information in the identification means.

According to one aspect of the invention, the identification means comprises a scannable code on a lid of each of the pharmaceutical containers.

According to another aspect of the invention, the scanning means comprises a scanner mounted on an underside of the closeable top cover.

According to another aspect of the invention, the scanning means comprises a camera adapted to take a photograph when the closeable top cover is in a closed position and the computer executable instructions include image processing instructions for interpreting information from the photograph.

According to another aspect of the invention, there is provided a plurality of load cells positioned at a base of the housing; each of the pharmaceutical containers positioned on a respect load cell; wherein the load cell is in communication with the computer system to provide weight data for each of the pharmaceutical containers to the computer system.

According to another aspect of the invention, there is provided a graphical user interface on an outer surface of the housing.

According to another aspect of the invention, the graphical user interface includes a touch screen for activating various processes to be executed by the computer processor.

According to another aspect of the invention, there is provided a scan trigger connected to the closeable top cover for indicating a closed position of the cover and activating the scanning means.

According to another aspect of the invention, there is provided a web-enabled camera and microphone in communication with the computer processor; the system further comprising a network interface to provide network communications to the computer processor and enabling web-based communications via the camera and the microphone.

According to another aspect of the invention, the computer executable instructions include instructions for determining when one of the plurality of pharmaceutical containers is empty based on a known weight of an empty container compared to the measured weight provided by the load cell.

According to another aspect of the invention, the computer executable instructions further include instructions for providing a notification to refill a prescription based on the empty container.

According to another aspect of the invention, the computer executable instructions include instructions for determining whether a pharmaceutical has been removed from one of the plurality of pharmaceutical containers by comparing a weight of one of the pharmaceutical containers to a previously stored weight of one of the pharmaceutical containers.

According to another aspect of the invention, the computer executable instructions further include instructions for providing a notification to a user if a scheduled prescription administration has been missed; wherein a schedule of prescriptions due to be administered is stored on the computer readable medium.

According to another aspect of the invention, the computer executable instructions further include instructions for upon detecting that a scheduled prescription administration has been missed, providing a notification to the user.

According to another aspect of the invention, the computer executable instructions further include instructions for alerting an emergency contact if a state of the schedule prescription administration being missed persists for more than a pre-determined period of time; wherein the emergency contact information is stored on the computer readable medium.

According to another aspect of the invention, the graphical user interface provides information on the plurality of prescription containers.

According to another aspect of the invention, the web-based communications comprises web-based communications with a pharmacist; wherein contact information for the pharmacist is stored on the computer readable medium.

According to another aspect of the invention, the web-based communications comprises communications with an emergency contact; wherein contact information for the emergency contact is stored on the computer readable medium.

DETAILED DESCRIPTION OF THE EMBODIMENTS

Figure 1:
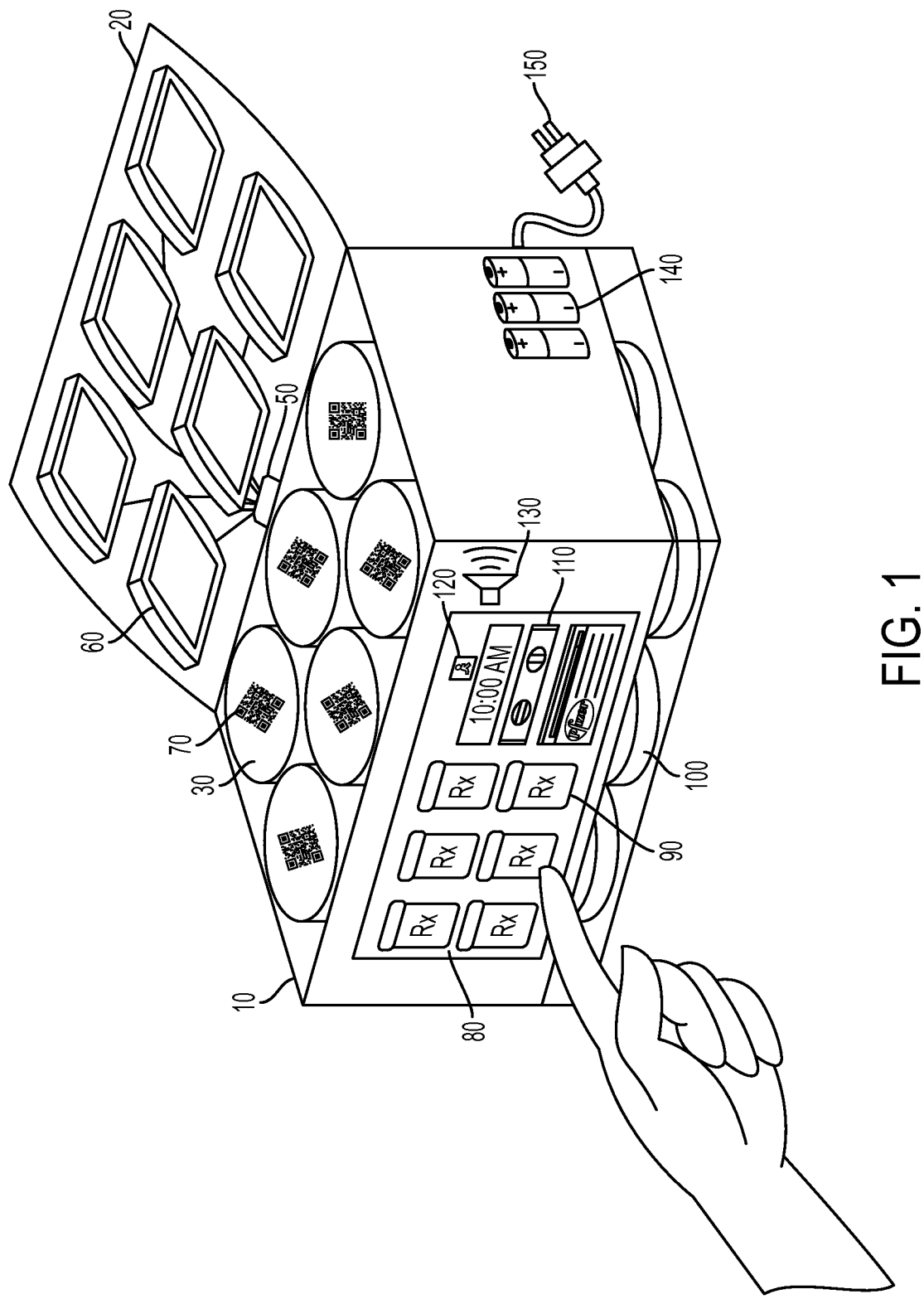
FIGS. 1 and 2 show two embodiments of a system according to the invention.

Referring now to FIG. 1, there is shown one embodiment of the invention, in which the pharmaceutical dispensing and management system of the invention is shown. The system is generally contained within a housing 10, having a cover 20 that may be opened to provide access to the interior of the housing 10. The housing 10 is preferably formed from a plastic material, but other materials are also contemplated. Preferably, the housing 10 is lightweight, high strength, portable and waterproof thereby making it suitable for a variety of uses.

Within the housing 10, there are located a plurality of pharmaceutical containers 30 holding medications therein. While these will typically be prescription medications, it is also possible that other types of may be included as well, such as supplements to counter the side effects of particular prescription medications and other non-prescription drugs or supplements recommended by a medical professional. For the purposes of this application, all references to pharmaceuticals are considered to include supplements, vitamins and other orally administered medical or pseudo-medical pills. The containers 30 are fixed in position by a retaining means, which in the illustrated embodiment are a plurality of bin separators 40. The bin separators 40 ensure that the containers 30 do not move around within the housing 10, to ensure functioning with the scanning system, described below. Furthermore, the bin separators 30 provide for visible organization of the containers 30 within the housing 10 and can also be used to implement colour-coded schemes in regards to parts of the housing 10 that contain particular types of pharmaceuticals. The containers 30 may also have various indicia, labels or other markings thereon identifying the pharmaceutical within the container, or providing any other information related to the prescription.

Of particular note in regards to indicia, a label 70 may be provided on a top surface of the container 30. These labels are preferably QR codes that include a large storage of alphanumeric characters which can be printed or otherwise identified in high densities, with small sizes and have some degree of data validation or error correction. Provided on the cover 20 is a scanning engine 60 that may communicate with a computer system 110 (discussed below) to capture and interpret information on the labels 70. The scanning engine 60 is preferably relatively small in size so that it can readily be integrated within the cover 20, and provides for fast and accurate scanning and interpretation of the data on the labels 70. Various off-the-shelf scanners may be used. In one alternative, the scanning engine 60 may consist of a camera taking a photograph of the labels, where the photograph is processed by software executed on the computer system in order to read the labels. It is contemplated that such software may be of the sort found on mobile device application, which use images taken by a camera to read bar codes, and similar identifying materials.

A scan trigger means 50 is also provided to initiate scanning of the label 70 when the cover 20 is in the closed position. The trigger means 50 may be a sensor that detects when the cover 20 is in the closed position, or may alternatively have a degree of intelligence built into it when communicating the with computer system 110 such that scans are periodically triggered, or only triggered in response to a pre-determined event, such as a user-initiated trigger.

A load cell 100 is provided on an underside of at least one of the containers 30, and preferably under each of the containers 30. The load cell 100 is configured to weigh, or otherwise evaluate, the contents of the container 30, while the computer system provides an indication of how many pills are remaining in the container 30. The load cells 100 are also connected to the computer system 110 which processes all this information. For example, the weight of an empty container is known, as is the weight of a container full of pills along with the weight of an individual pill. Using the weight measured by the load cells 100, the number of pills remaining in one or more containers 30 can readily be calculated as this information is passed on to the computer system.

The computer system 110 is used to interpret, evaluate, compute, integrate and store information obtained from the various features of the system as herein described. Furthermore, the computer system 110 controls the scanning engine 60 the load cell 100 and communicates with any third parties via a network interface. The computer system has a number of physical and logical components, including a central processing unit ("CPU"), random access memory ("RAM"), an input/output ("I/O") interface, a network interface, non-volatile storage, and a local bus enabling the CPU to communicate with the other components. RAM provides relatively-responsive volatile storage to the CPU. The I/O interface allows for input to be received from one or more devices, as described above, and may also provide for data to be received from a touch screen or a detachable keyboard. The I/O interface also outputs information to output devices, such as a display and/or speakers. The network interface permits communication with other systems. Non-volatile storage stores the operating system and programs, including computer-executable instructions for implementing various features of the invention as herein described.

Computer software executed by the computer system 110 may provide for integrating a pharmacy user with prescription data and the QR code to create print-ready labels for the containers. Information may also be stored in database that is preferably independent of the platform and system used such that data can be transferred or communicated to other systems as needed. Software is also provided to display key pill prescription information, and is preferably user-friendly, provides real-time data updates, visual data illustrations, colour interpretations, resizable fonts, and various customizations to assist users with various medical conditions. Finally, advertising may also be provided on the interface, including promotions available to system users only. Regulatory and administration information may also be displayed. Multi-language support is also provided, along with volume controls, voice activation and dictation to assist different user capabilities.

The touch screen 90 displays a graphical user interface, and is also adapted to accept user input. The interface may display information related to the pill containers, configurations, system settings, warnings of pharmaceuticals running out, and other system related warnings that may be beneficial to a user or to the proper functioning of the system. Warnings may also be used to alert users to actionable events, and may be in the form of visual or audio queues.

Power is provided via power interface 150, or alternatively, an on-device battery pack 140 may be provided for emergency power loss situations, or when traveling away from a home position.

The system of FIG. 1 may be assembled or put together using standard mechanical and/or electrical equipment, fasteners and techniques generally available in the art. The invention lies in the combination of elements provided within the housing and their interactions with each other to provide the pharmaceutical management system, rather than in the particular mechanical design of the housing itself. Furthermore aspects of the invention provide for the methods and processes enabled by the system as described.

Figure 2:
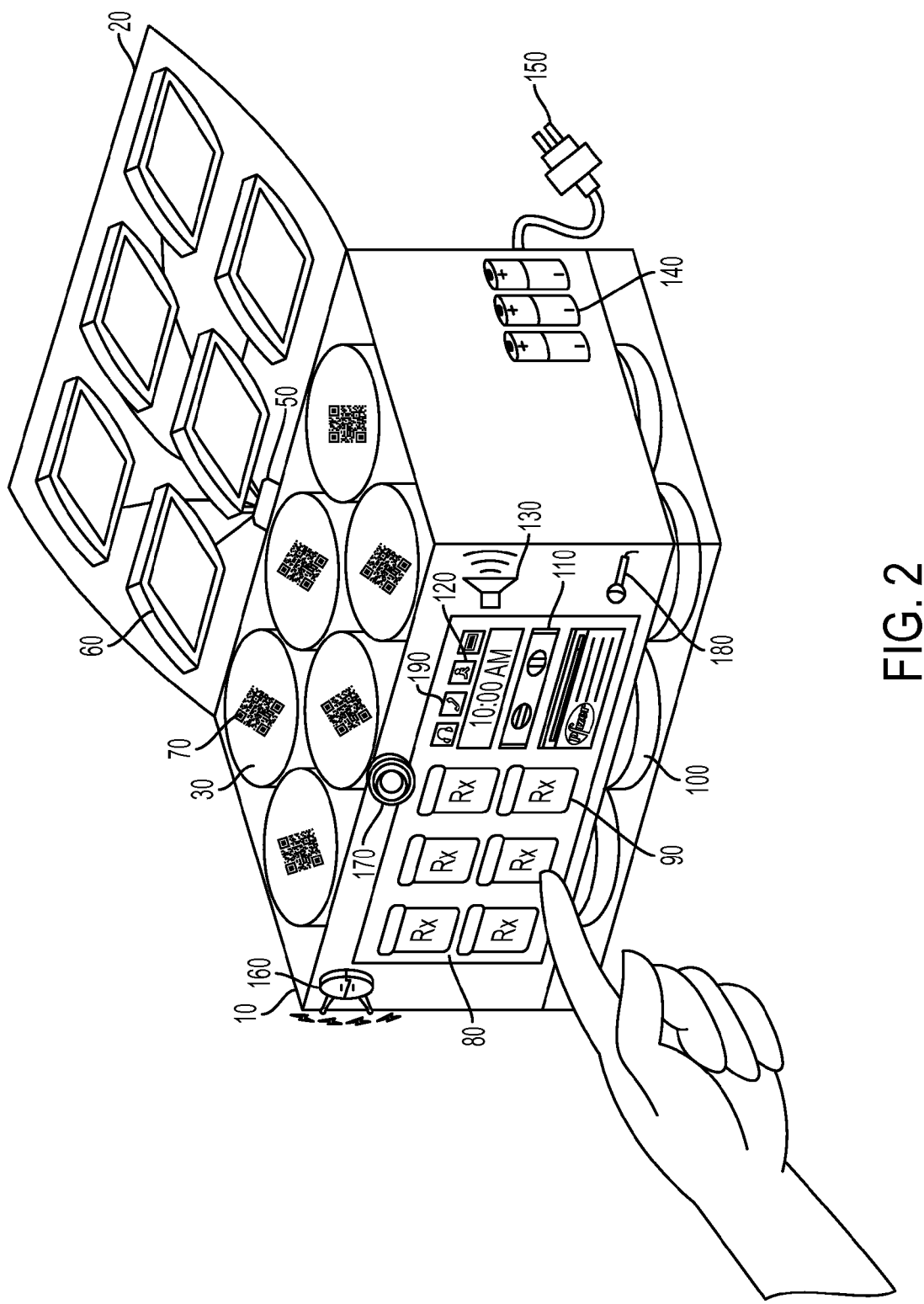

FIG. 2 shows a system according to another embodiment of the invention in which the system further includes audio and/or video communication capabilities, such as a camera and microphone. This permits teleconferencing abilities with a video pharmacist with two-way communication between the end user and the pharmacist. A locking mechanism may also be implemented such that a user name, password or other digital type security key is required to access the individual pill containers.

Figure 3:
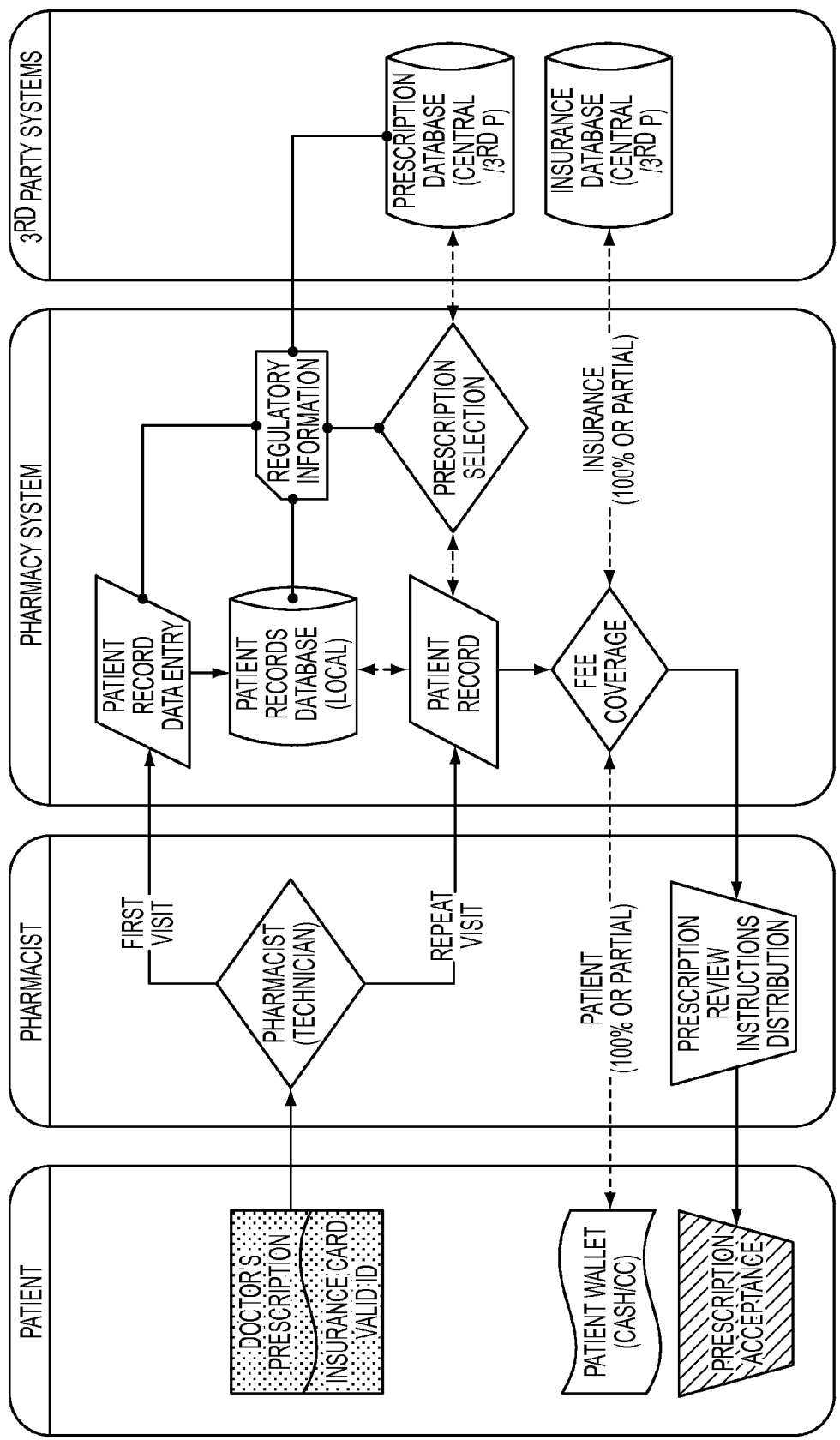
FIGS. 3, 4, 5A, 5B, 6, 7, 8, 9, 10, 11A and 11B show various processes enabled by the system of FIGS. 1 and 2.

FIG. 3 illustrates the involvement of various parties leading up to the acquiring of relevant pharmaceuticals by a patient for use in the system of FIGS. 1 and 2. As shown, a patient has a doctor's prescription and takes this to the pharmacy, where the pharmaceutical is dispensed. If this is the first time a prescription is being filled, a patient database entry is created on a database associated with a pharmacy computer system. The pharmacy database could include personal information of the patient, drug plan information, as well as detailed prescription information. The pharmacist then reviews the prescription, issues the medication and the user (or with the help of the pharmacist) loads the containers of the device as illustrated in FIGS. 1 and 2. Payment processing may be handled by third party operators that could include considerations for drug insurance plans. These types of payment processors are widely known and not described in further detail. Optionally, the database may be provided to or managed by a third party system so that information can be accessed remotely and from any device.

Figure 4:
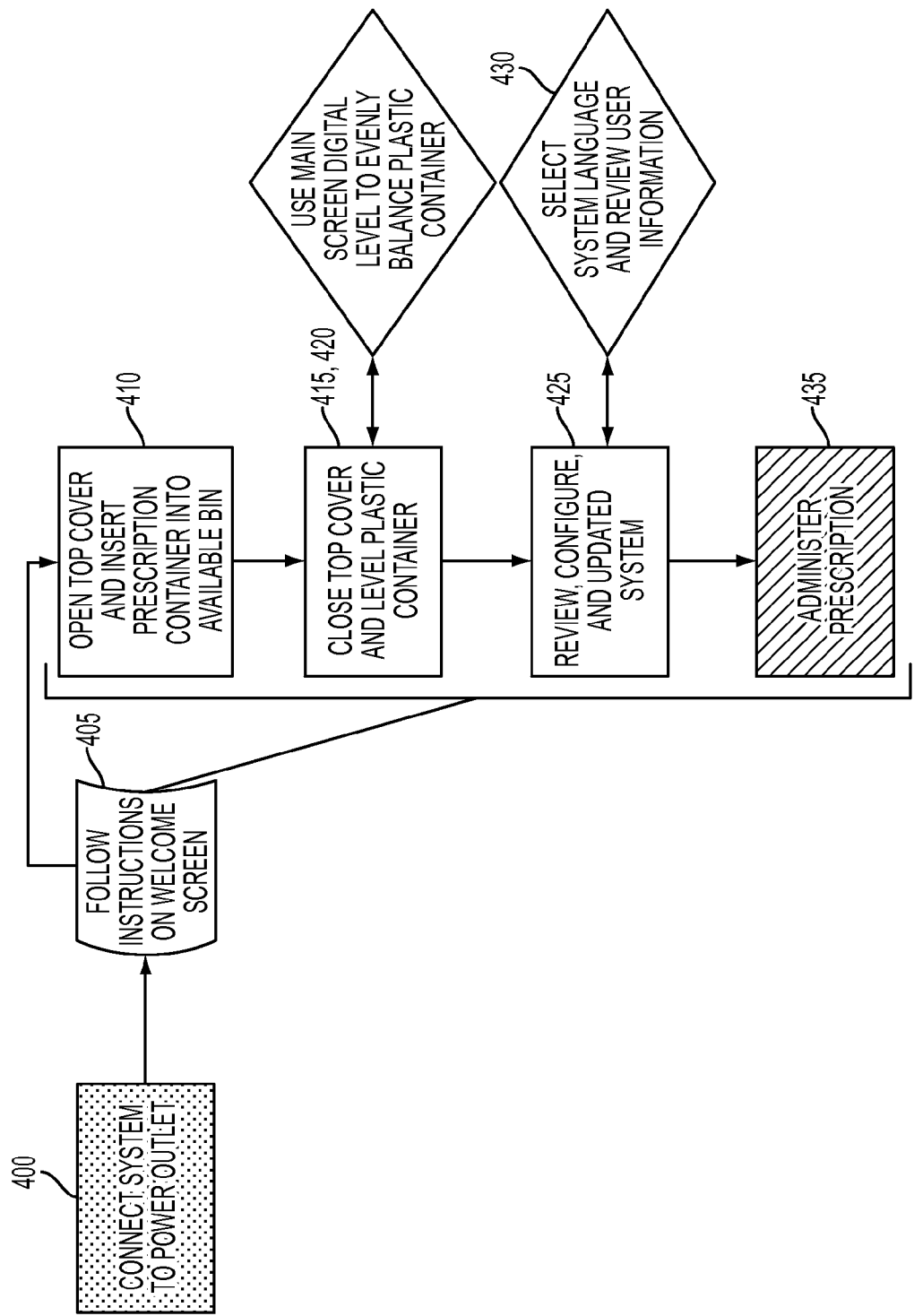

FIG. 4 shows an exemplary setup of the system of FIGS. 1 and 2 for first time use. After connecting to power at step 400, on-screen welcome information and instructions are shown at step 405. The user would then open the cover on the housing and insert the prescription containers into the housing at step 410. The top is closed at step 415, and the labels on the containers are read by the scanner to populate a database on the computer for the first time at step 420. System settings and user preferences can also be set at steps 425 and 430, such as language of use and patient details. The user would also have the option to call a toll free number for first time initiation/setup of the system with their details, as well as the setup of various available plans (e.g. Pharmacist Dial Anytime Plan, 1×month, etc. . . . ) Moreover, the system is periodically populated or updated with the latest drug compatibility data, with the consideration that an initial version of this data will be installed at the factory. This updating may occur via a network or wireless network connection with the system of FIG. 1. Finally, at step 435 the prescription can be released or an indication given for the user to take a prescription from a specified container in the system.

Figure 5A:
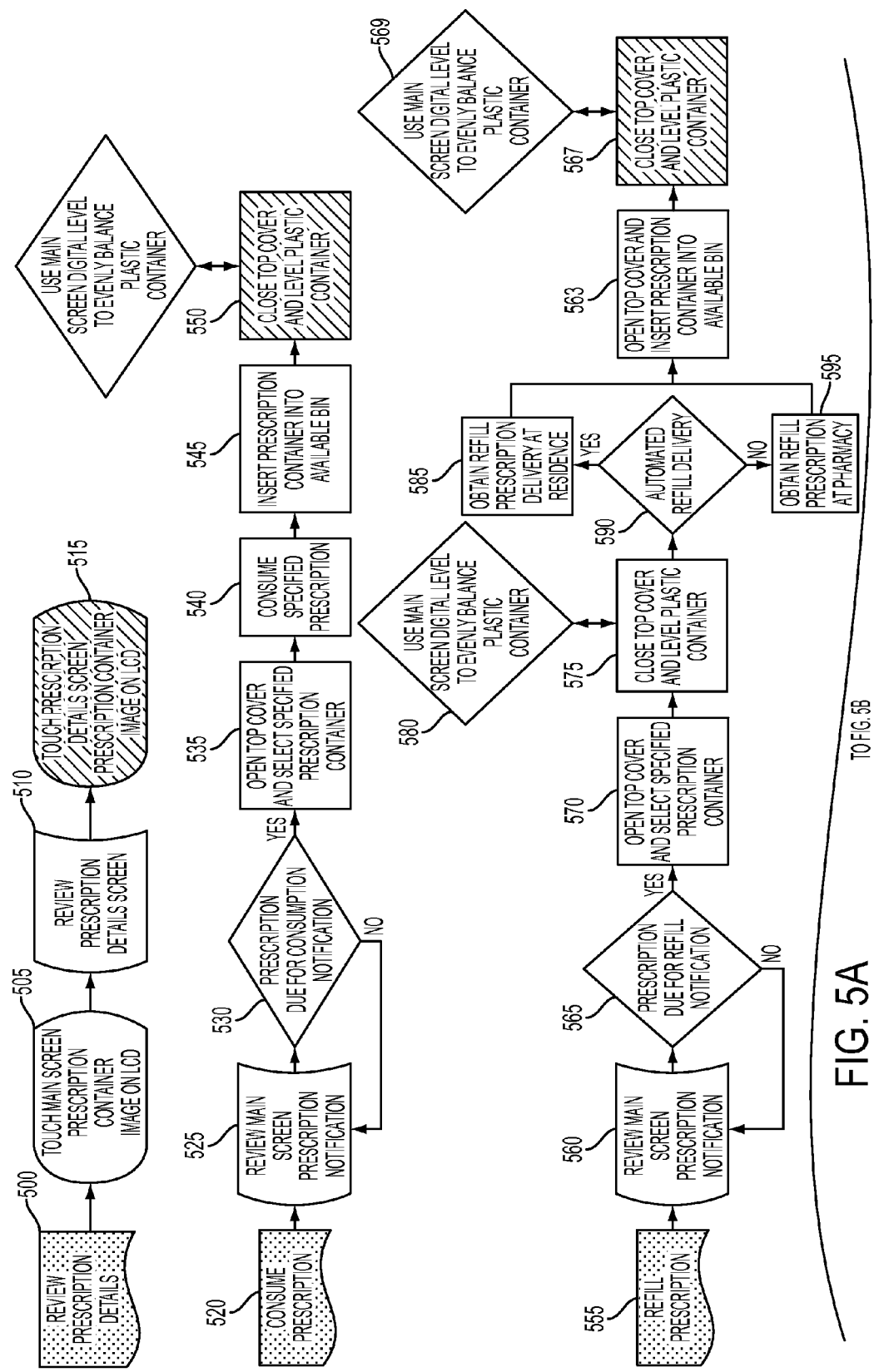
Figure 5B:
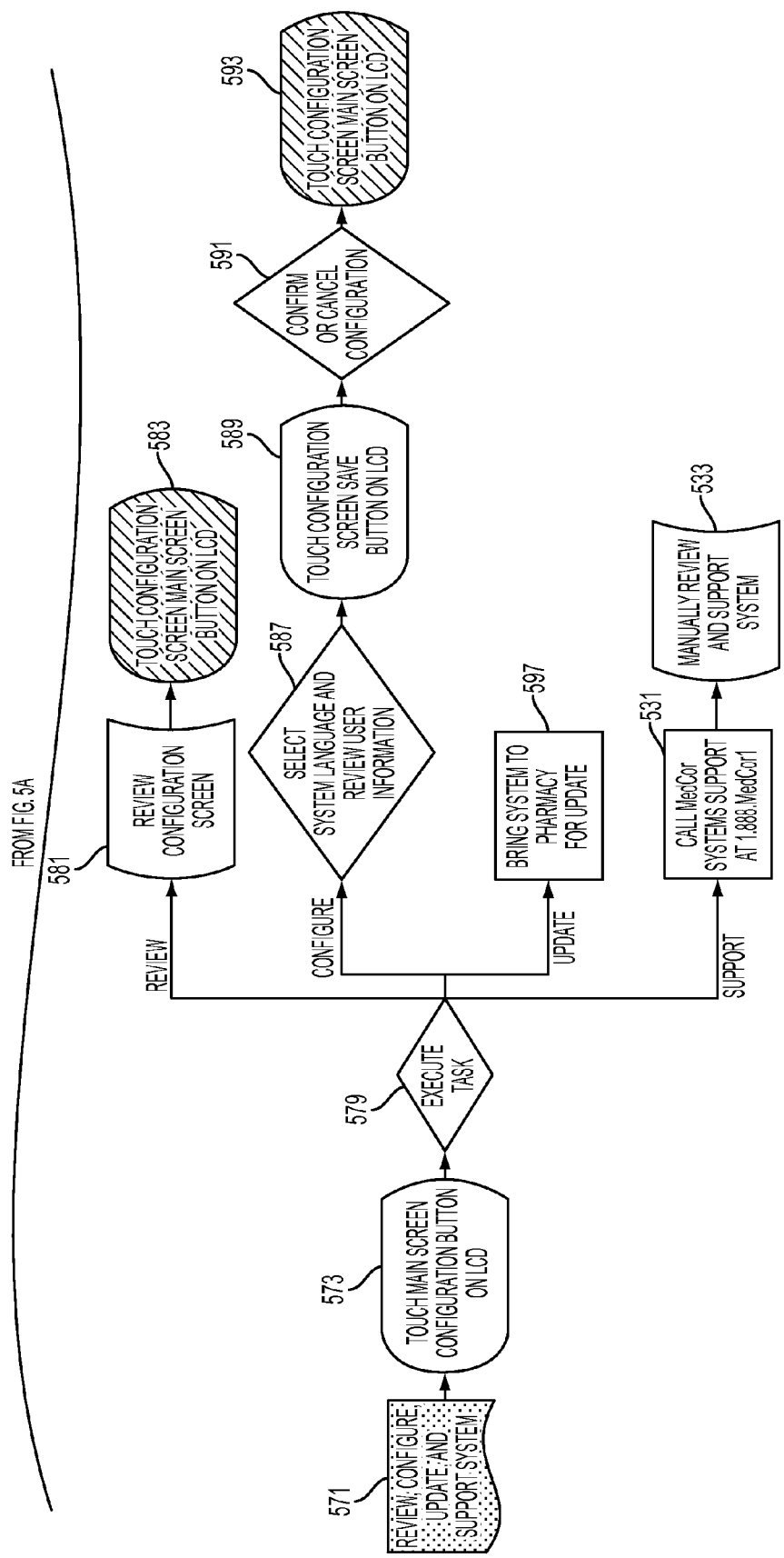

FIGS. 5A and 5B show the various steps involved detailed use of the system and processes enabled by the system as herein disclosed.

One functionality provides for a review of prescription details 500. The graphical user interface described in FIG. 1 may be a touch screen displaying images of each of the containers within the system. A user would touch the specific container at step 505, which would trigger a display of the prescription details associated with that particular container at step 510, with additional details on the prescription being made available when specific portions of the screen are touched at step 515.

In order to consume a prescription pill at step 520, the user reviews the graphical user interface for a prescription notification 525. Alternatively, an alarm may be provided which gives audible notification so a user does not have to regularly check the screen for an active notification. In any case, if a notification is present as determined at step 530, the user opens the top cover and selected specified prescription container at step 535. The prescription is self-administered or consumed at step 540, and the container returned to its relevant bin at step 545. The cover is of the container and of the housing are then closed at step 550, and the computer system determines the weight of each of the containers to reassess the number of pills remaining in each of the containers.

A refill prescription process flow is shown at step 555, where the user reviews the graphical user interface at step 560 for a prescription due for refill notification. If such a notification is present at step 565, the user opens the cover and identifies the container in need of a refill at step 570, based on information provided in the graphical user interface. The cover is then closed at step 575, with the computer system identifying which container has been removed by its interaction with the scales at step 580. Refill of the container with the appropriate prescription may occur by way of automated delivery, in which the computer system communicates with a computer system at a pharmacy to indicate a refill is necessary and appropriate arrangements are made to deliver the prescription to the user's residence at step 585, or alternatively, the user attends the pharmacy in person to refill the prescription at step 595. The computer system may provide an indication of the type of delivery being made by notification to the user at step 590. The user then replaces the filled container at step 563, closes the cover at step 567 and the computer system assesses the number of pills in the refilled container as previously described at step 569.

Next, and as shown in FIG. 5B, the software executing computer system may be configured and/or updated as per step 571. An update button is provided on the touchscreen, which can be activated by the user or by a technician at step 573. A selection of the specific task is made at step 579, relating to reviewing the current configuration, configuring the system, updating the system or activating customer support. In reviewing the configuration at step 581, the user selects a review configuration button or series of buttons at step 583. In the configure option, the user selects the system language and reviews/updates user information at step 587, the configuration can be saved at step 589, with an option confirmation notification provided at step 591 and an end to the process at step 593. In the update mode, a single option update is provided at step 597, where updates are provided via the network interface of the computer system. A call support function can be provided by a button directly on the housing and activated at step 531, with support being provided at step 533.

Figure 6:
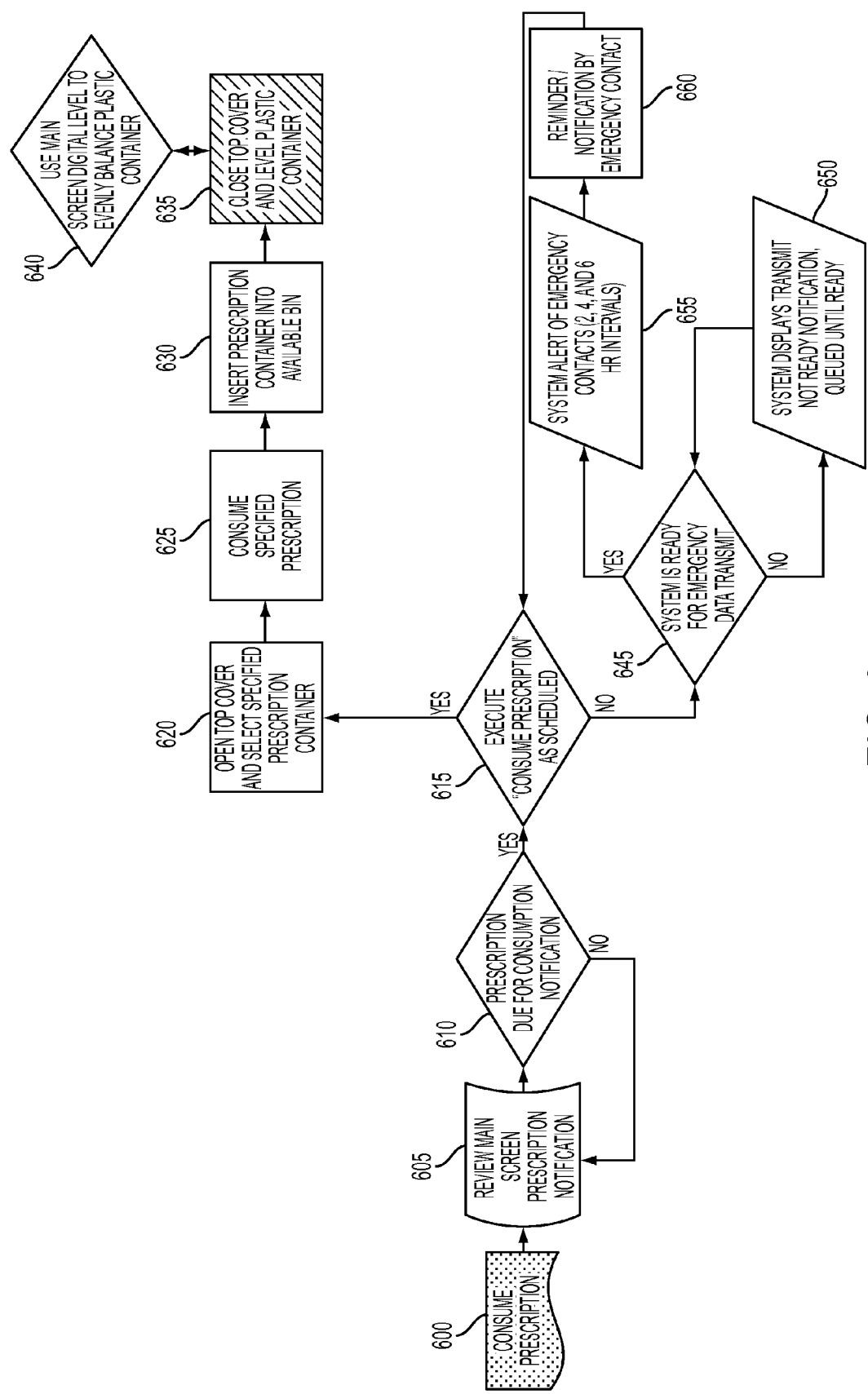

FIG. 6 shows an optional emergency warning system that can be implemented, wherein if the system detects that a scheduled prescription has not been taken within a specified time period, an emergency alert is sent to a predetermined contact person, and particular intervals. Periodical reporting is also sent to predetermined contacts, as per settings. The user can then be reminded by the emergency contact to take the prescription, or can otherwise be checked up on to ensure that the user is not suffering a medical emergency. In FIG. 6, steps 600, 605 and 610 are as has been described with respect to FIG. 5A. At step 615, a determination is made as to whether a prescription has been taken as scheduled. If the user acknowledges the prescription notification, and consumes the prescription, steps 620, 625, 630, 635 and 640 are carried out as has been described in FIG. 5A. If the system detects that no pill has been taken, for example by executing the weighing of each of the containers as described above, a predetermined grace period is provided within which the system prepares to transmit an emergency signal. The grace period is provided in the event the user is marginally late in taking the prescription. A check is made to determine whether the grace period has expired at step 650. If not, the system maintains its ready status and loops with step 650 at predetermined intervals. Once the grace period has passed a notification is sent to one or more emergency contacts at step 655, followed by subsequent notifications to emergency contacts at step 660. The process returns to step 615 in a loop fashion until the prescription is taken. Notifications to the emergency contacts may be executed by way of automated telephone call, text message or email.

Figure 7:
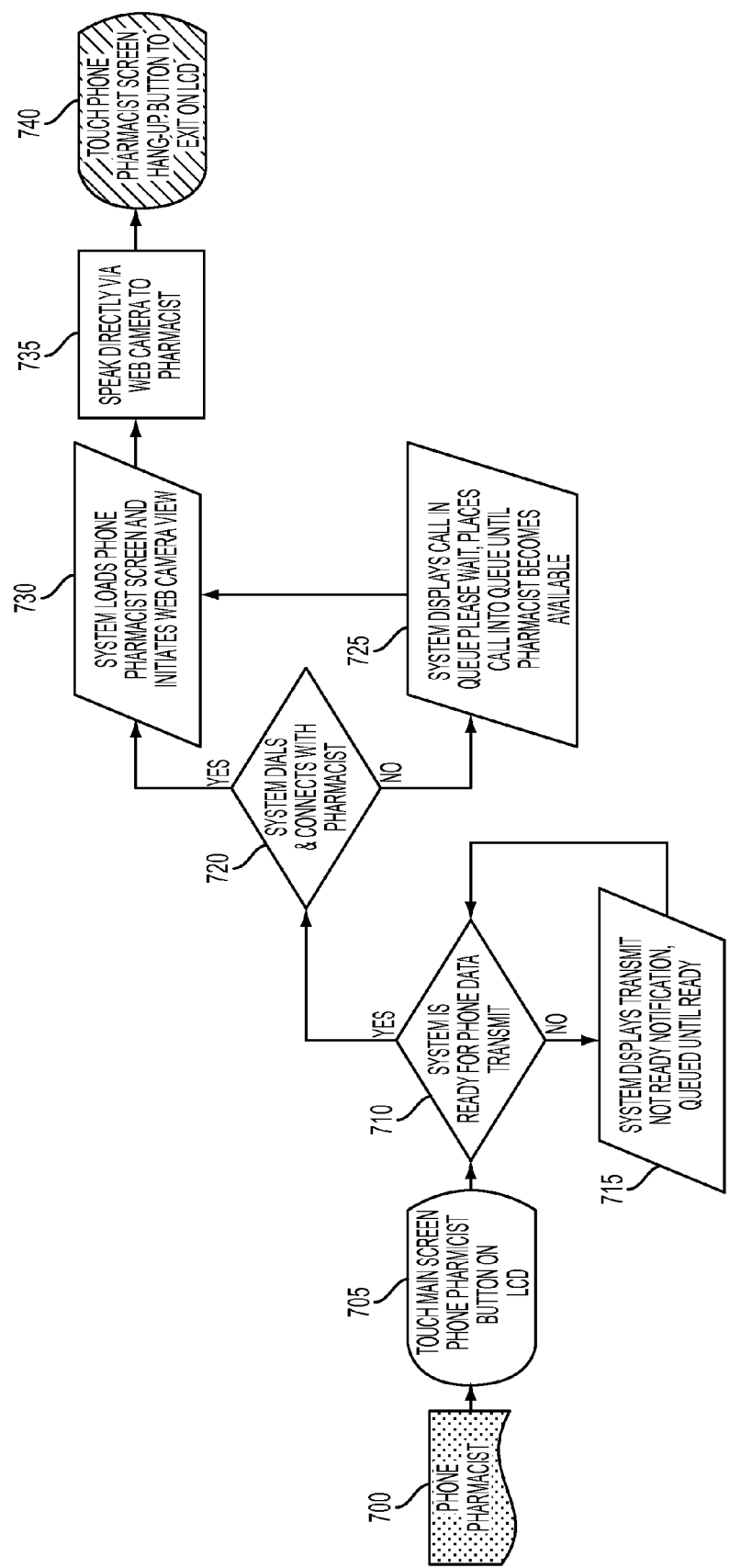

FIG. 7 illustrates a typical process where a pharmacist is contacted by the web camera and microphone of the system as illustrated in FIG. 2. The user initiates a phone pharmacist function at step 700 by touching on the appropriate button on the touch screen at step 705. If the system is ready for phone data transmission at step 710, the call is placed to the pharmacist at step 720. If not, the system provides an indication that phone transmission is not ready at step 715 and attempts to try again after a predetermined time period. If the pharmacist is available, the call is initiated and the webcam activated at step 730. The user speaks directly to the pharmacist at step 735 and can terminate the call at step 740. If other users are also simultaneously contacting the pharmacist, or if the pharmacist is unavailable, a queue is generated at step 725 to place the call into the queue until the pharmacist is available, where the process resumes at step 730

Figure 8:
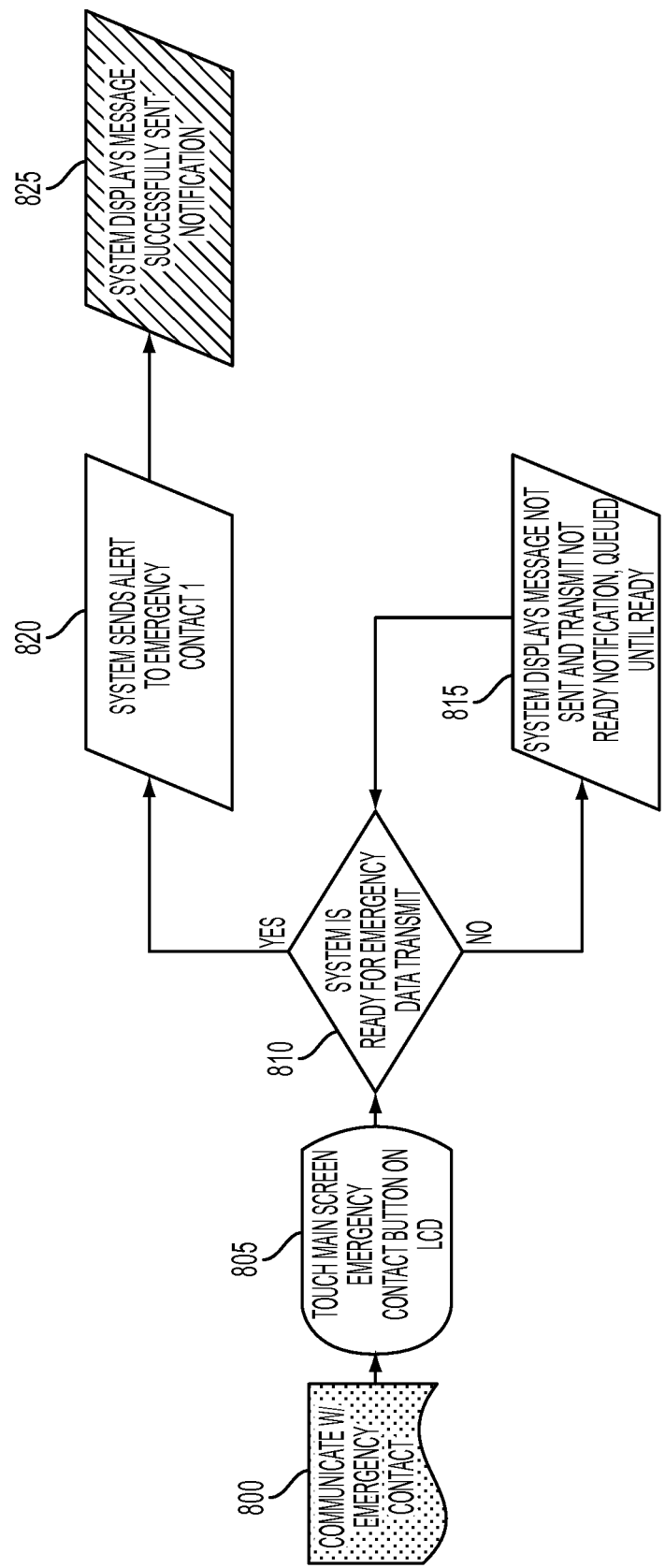

FIG. 8 shows a sub-process for user-initiated communication with an emergency contact 800. The user may touch a contact button on the screen at step 805, and a determination is made as to whether the system is ready for communication at step 810. If the system is not ready for communication, a notification is provided and a redetermination is made after a predetermined time period at step 815. Once the system is ready, an alert is sent to an emergency contact at step 820 and a message provided of a successful completion of the notification at step 825.

Figure 9:
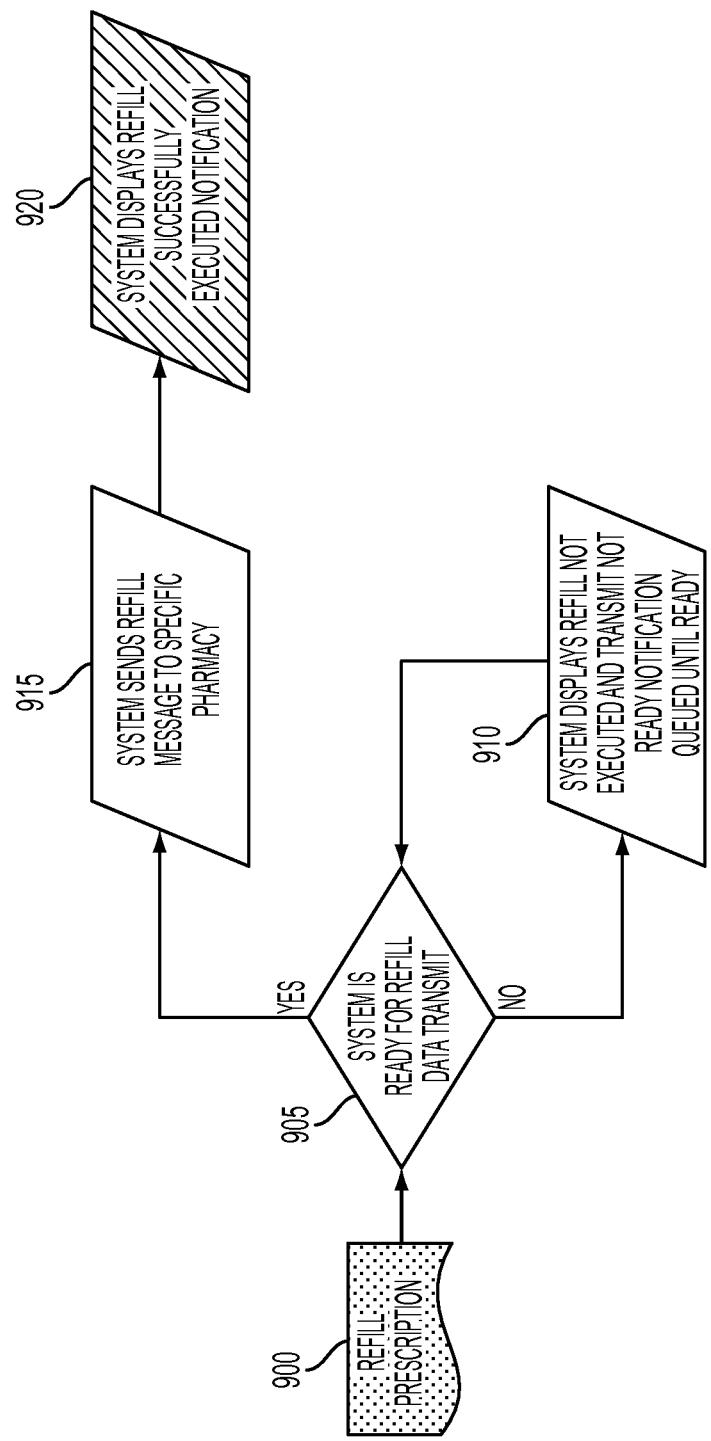

FIG. 9 shows a sub-process for automatic refill of a prescription 900. The computer system determines whether one of the prescription containers is ready for a refill at step 905. If not, a redetermination is made after a predetermined time period at step 910. If the system is ready to transmit the refill communication, a message is sent to a predetermined pharmacy at step 915 and a refill procedure is executed at 920, which may include initiating delivery of the prescription to the user's home.

Figure 10:
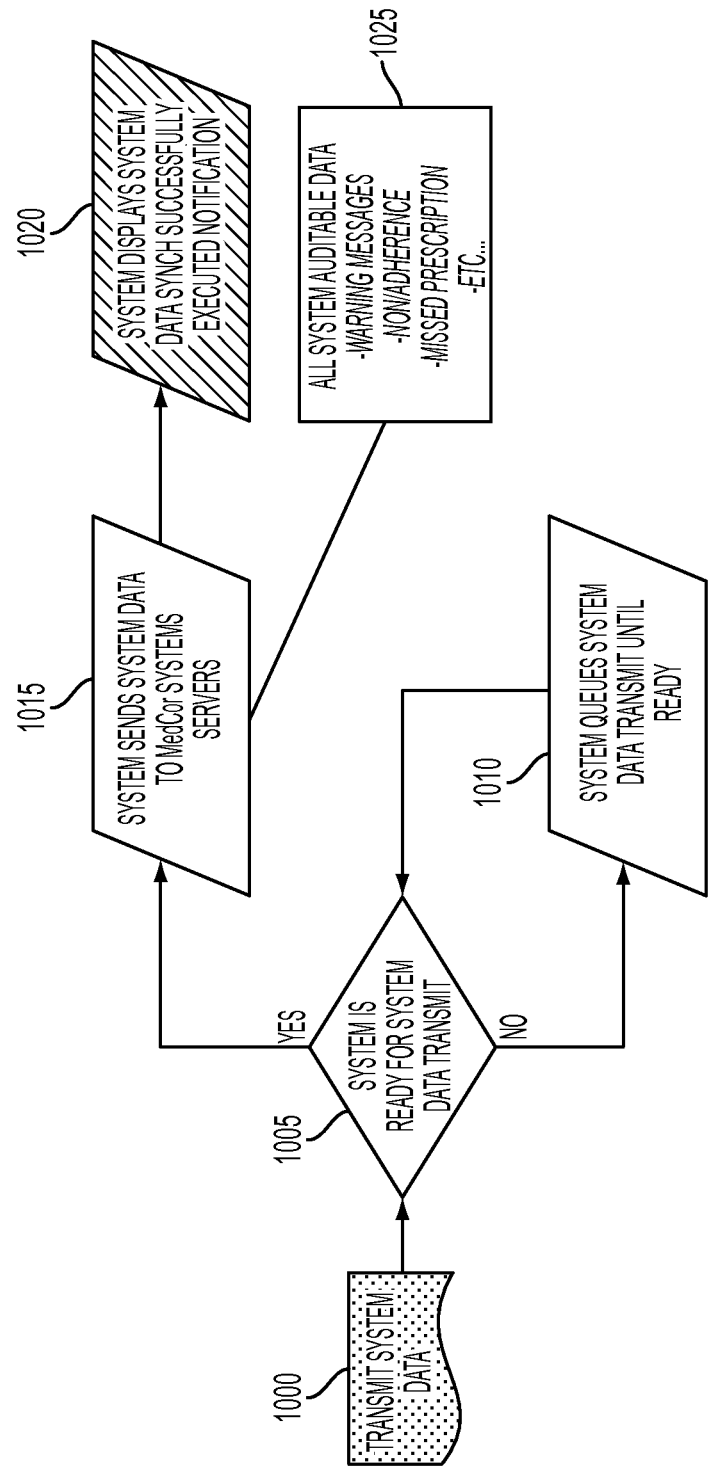

FIG. 10 shows a general transmission of data sub-process 1000, for example for the purposes of determining whether the system is functioning properly. If data is ready to be transmitted at step 1005, such data is sent to a service provider's servers at step 1015, and an indication of successfully completed communication is provided at step 1020. Various alerts may also be provided to the user at step 1025. If data is not ready to be transmitted, a queue is prepared at step 1010 and checked against until the system is ready for data transmission.

Figure 11A:
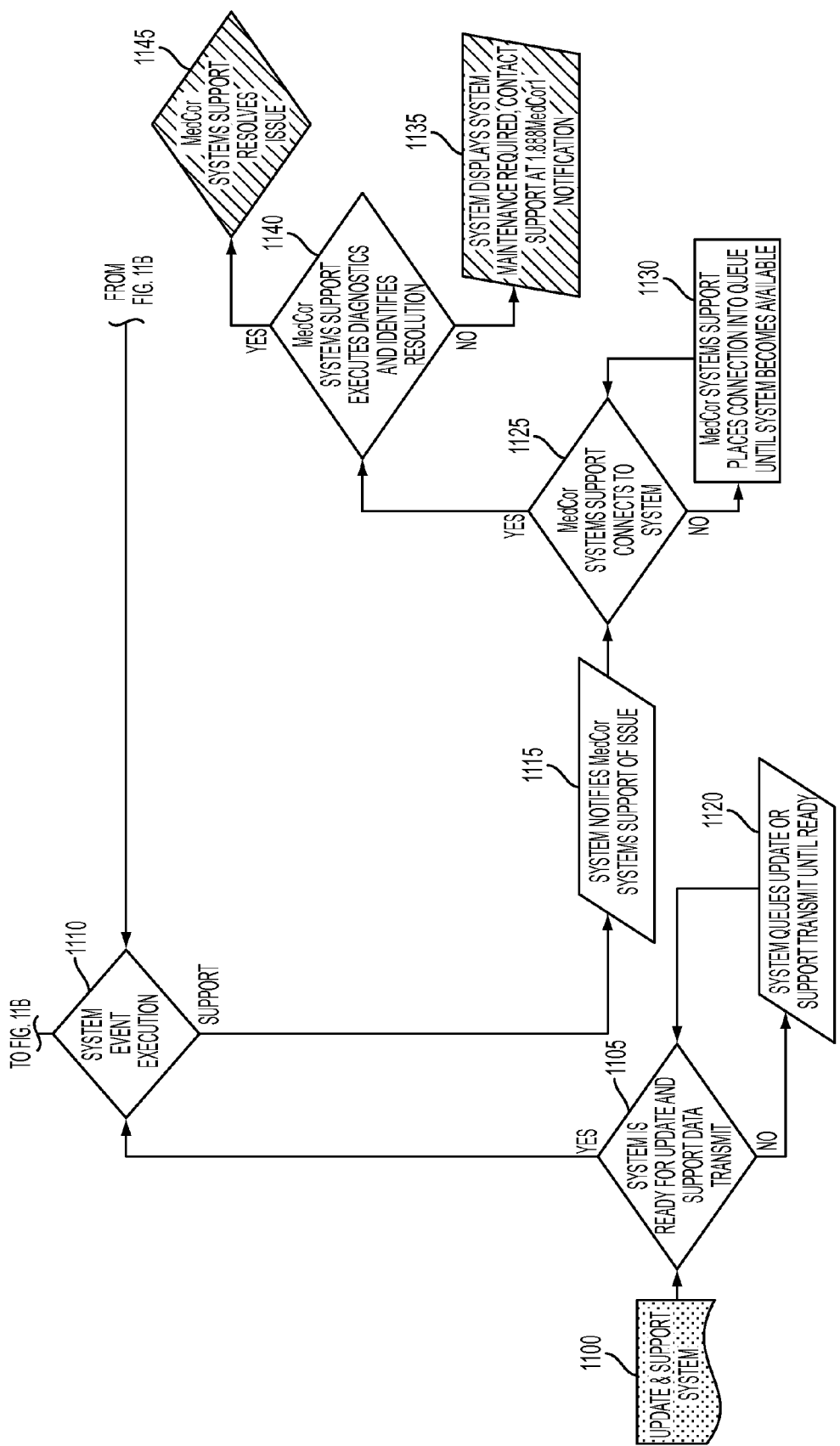
Figure 11B:
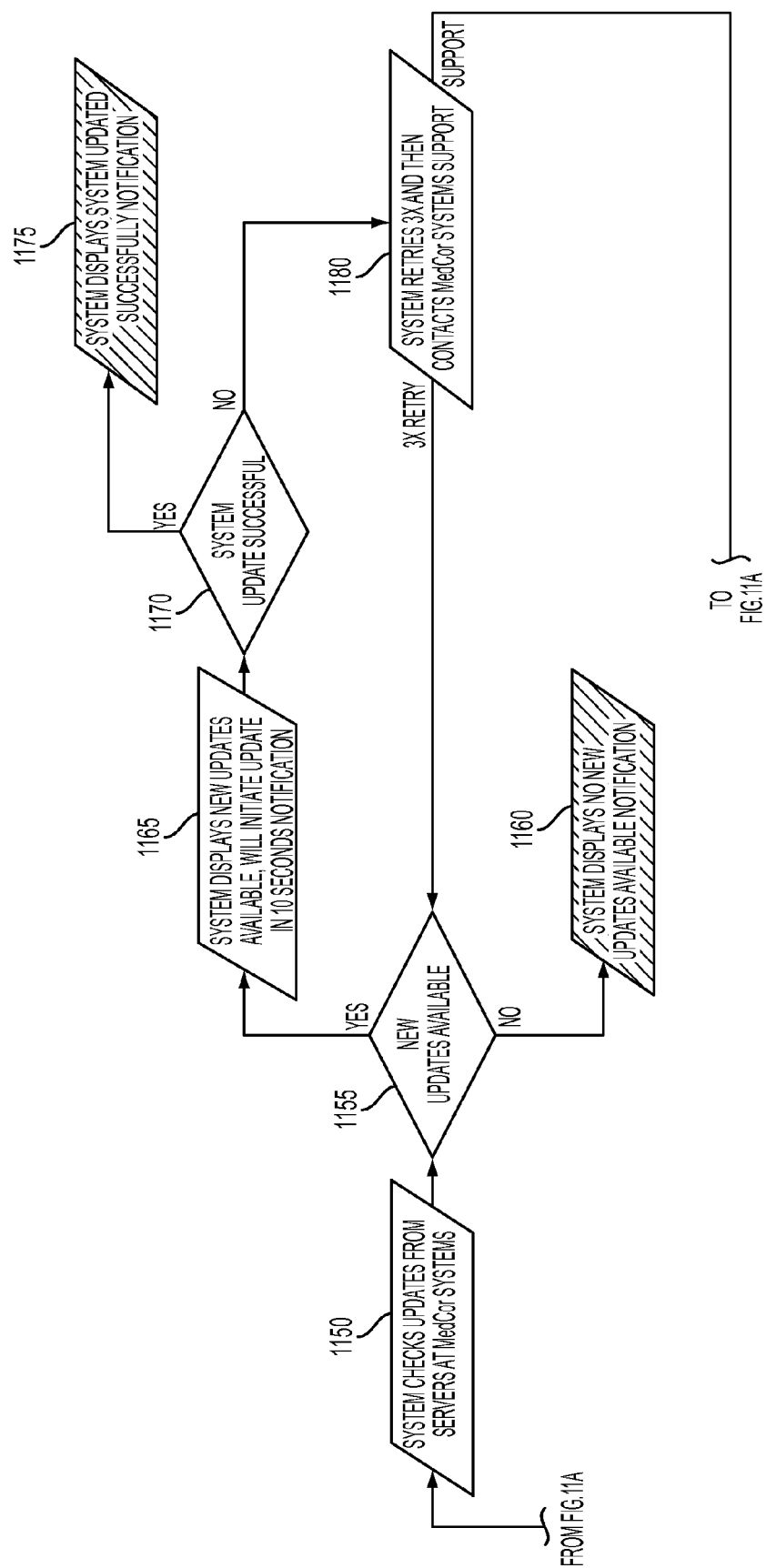

FIGS. 11A and 11B shows a workflow for updating the software of the computer system at step 1100. If an update is available and ready as determined at step 1105, an update event is executed at step 1110. If not, a redetermination is made after a predetermined time period at step 1120. Once the update event is executed, the system checks for updates from the service provider's services at step 1150. If no update is available, a notification is sent at step 1160. If an update is available, a notification is provided at step 1165 and an update initiation time is given. The updated software is then downloaded and installed. If the update is determined to be successful at step 1170, a notification is provided at step 1175. If the update is not successful, another attempt is made at step 1180. If the update cannot be completed, a notification is sent to the service provider at step 1115, where a remote connection to the system is provided at step 1125. A diagnostic is run at step 1140 to determine the problem and identify a resolution. The issue is then resolved at step 1145. If the resolution cannot be identified, further maintenance may be required and a notification to this effect is provided at step 1135.

It is understood that the system as herein described may be used at a user's home, in a hospital, retirement home or any other location. The foregoing description is meant to be illustrative of specific embodiments only, with the invention not limited to such specific embodiments, but solely by the claims that now follow.

The invention claimed is:

1. A pharmaceutical management system comprising a housing having
    a closeable top cover; the pharmaceutical management system including within said housing, in combination:
    a computer processor and a computer readable medium storing computer executable instructions being executed by said computer processor;
    a plurality of pharmaceutical containers within said housing; each of said plurality of pharmaceutical containers having a scannable code on a lid thereof;
    a plurality of load cells positioned at a base of said housing, each of said pharmaceutical containers positioned on a respective load cell, wherein said respective load cell is in communication with said computer processor to provide weight data for said each of said plurality of pharmaceutical containers to said computer system;

a scanner mounted on an underside of said closeable top cover, and in communication with said computer processor adapted to read information from said scannable code, said scanner comprising a camera adapted to take a photograph when said closeable top cover is in a closed position;

a scan trigger connected to said closeable top cover for indicating a closed position of said cover and activating said scanner;

a touchscreen on an outer surface of said housing; and wherein said computer executable instructions include instructions for:

identifying a pharmaceutical in each of said containers based on information in said scannable code;

determining a number of pills remaining in each of said plurality of containers based on said weight data, the weight of an empty container, and the weight of a single pill in each of said plurality of containers;

displaying on said touchscreen an image of each of said plurality of pharmaceutical containers; and displaying prescription details associated with a particular container in response to a user touching the respective image of the particular container.

2. The pharmaceutical management system according to claim 1, wherein said computer executable instructions include image processing instructions for interpreting information from said photograph.

3. The pharmaceutical management system according to claim 1, further comprising a web-enabled camera and microphone in communication with said computer processor; said system further comprising a network interface to provide network communications to said computer processor and enabling web-based communications via said camera and said microphone.

4. The pharmaceutical management system according to claim 1, wherein said computer executable instructions include instructions for determining when one of said plurality of pharmaceutical containers is empty based on the weight of an empty container compared to the weight data provided by said load cell.

5. The pharmaceutical management system according to claim 4, wherein said computer executable instructions further include instructions for providing a notification to refill a prescription based on said determining.

6. The pharmaceutical management system according to claim 1, wherein said computer executable instructions include instructions for determining whether a pharmaceutical has been removed from one of said plurality of pharmaceutical containers by comparing the weight data of one of said pharmaceutical containers to a previously stored weight of said one of said pharmaceutical containers.

7. The pharmaceutical management system according to claim 6, wherein said computer executable instructions further include instructions for providing a notification to a user if a scheduled prescription administration has been missed; wherein a schedule of prescriptions due to be administered is stored on said computer readable medium.

8. The pharmaceutical management system according to claim 7, wherein said computer executable instructions further include instructions for alerting an emergency contact if a state of said schedule prescription administration being missed persists for more than a pre-determined period of time; wherein said emergency contact information is stored on said computer readable medium.

9. The pharmaceutical management system according to claim 1, wherein said touchscreen provides information on said plurality of prescription containers.

10. The pharmaceutical management system according to claim 3, wherein said web-based communications comprises web-based communications with a pharmacist; wherein contact information for said pharmacist is stored on said computer readable medium.

11. The pharmaceutical management system according to claim 3, wherein said web-based communications comprises communications with an emergency contact; wherein contact information for said emergency contact is stored on said computer readable medium.

12. The pharmaceutical management system according to claim 1, further comprising a locking mechanism that requires at least one of: a username, a password, and a digital type security key to provide access to the plurality of pharmaceutical containers.

13. The pharmaceutical management system according to claim 8, wherein said alerting an emergency contact comprises send an emergency signal.

14. The pharmaceutical management system according to claim 13, wherein said emergency signal is one of: an automated telephone call, a text message, and an email message.

15. The pharmaceutical management system according to claim 1, further comprising retaining means for said plurality of containers.

16. The pharmaceutical management system according to claim 15, wherein said retaining means comprise a plurality of bin separators.

17. The pharmaceutical management system according to claim 1, wherein said scannable code is a QR code.

* * * * *